(12) United States Patent
Iguchi

(10) Patent No.: US 9,024,278 B2
(45) Date of Patent: May 5, 2015

(54) QUANTUM-YIELD MEASUREMENT DEVICE

(75) Inventor: Kazuya Iguchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 65 days.

(21) Appl. No.: 13/988,778

(22) PCT Filed: Aug. 31, 2011

(86) PCT No.: PCT/JP2011/069838
§ 371 (c)(1),
(2), (4) Date: May 22, 2013

(87) PCT Pub. No.: WO2012/073568
PCT Pub. Date: Jun. 7, 2012

(65) Prior Publication Data
US 2013/0240754 A1   Sep. 19, 2013

(30) Foreign Application Priority Data
Nov. 29, 2010 (JP) .................. 2010-264853

(51) Int. Cl.
*G01J 1/58* (2006.01)
*G01N 21/64* (2006.01)
(52) U.S. Cl.
CPC .............. *G01N 21/64* (2013.01); *G01N 21/645* (2013.01); *G01N 2201/065* (2013.01)
(58) Field of Classification Search
CPC ................................. G01N 21/6458
USPC ....................................... 250/458.1
See application file for complete search history.

(56) References Cited

U.S. PATENT DOCUMENTS

| 4,645,340 A | 2/1987 | Graham et al. |
| 4,876,183 A | 10/1989 | Miyasaka et al. |
| 8,592,780 B2 | 11/2013 | Iguchi |
| 2002/0197740 A1 | 12/2002 | Hansen et al. |

(Continued)

FOREIGN PATENT DOCUMENTS

| CN | 101430278 | 5/2009 |
| CN | 101627288 | 1/2010 |

(Continued)

OTHER PUBLICATIONS

U.S. Office Action dated Jun. 5, 2014 that issued in U.S. Appl. No. 14/069,567 including Double Patenting Rejections on pp. 2-4.

(Continued)

*Primary Examiner* — David Porta
*Assistant Examiner* — Hugh H Maupin
(74) *Attorney, Agent, or Firm* — Drinker Biddle & Reath LLP

(57) ABSTRACT

A quantum-yield measurement device 1A comprises a dark box 5; a light generation unit 6, having a light exit part 7, for generating the pumping light L1; a light detection unit 9, having a light entrance part 11, for detecting the light to be measured L2; an integrating sphere 14, having a light entrance opening 15 for the light L1 to enter and a light exit opening 16 for the light L2 to exit; and a movement mechanism 30 for moving a sample container 3, the part 7, and the part 11 such that the container 3 attains each of a first state of being located inside of the sphere 14 and a second state of being located outside of the sphere 14 and causing the part 7 and part 11 to oppose the opening 15 and opening 16, respectively, in the first state.

4 Claims, 13 Drawing Sheets

(56) References Cited

U.S. PATENT DOCUMENTS

| | | |
|---|---|---|
| 2003/0120137 A1 | 6/2003 | Pawluczyk |
| 2004/0233428 A1 | 11/2004 | Hart et al. |
| 2010/0102238 A1 | 4/2010 | Kanazawa et al. |
| 2010/0108869 A1 | 5/2010 | Iguchi et al. |
| 2014/0097357 A1 | 4/2014 | Iguchi |

FOREIGN PATENT DOCUMENTS

| | | |
|---|---|---|
| CN | 101666680 | 3/2010 |
| JP | 7-83828 A | 3/1995 |
| JP | 7-120323 A | 5/1995 |
| JP | 10-73486 A | 3/1998 |
| JP | 2003-215041 A | 7/2003 |
| JP | 2006-125940 | 5/2006 |
| JP | 2007-086031 A | 4/2007 |
| JP | 2009-074866 A | 4/2009 |
| JP | 2010-151632 A | 7/2010 |
| JP | 2011-196735 | 10/2011 |
| JP | 2012-052821 | 3/2012 |
| WO | WO-2009/001846 A1 | 12/2008 |

OTHER PUBLICATIONS

Christian Würth et al., "Evaluation of a Commercial Integrating Sphere Setup for the Determination of Absolute Photoluminescence Quantum Yields of Dilute Dye Solutions," Applied Spectroscopy, Jul. 2010, pp. 733-741, vol. 64, No. 7.

Chang, L. I., et al., "Spectral Power Distribution and Quantum Yield in $Ce^{3+}$-Doped Glass-Ceramics,"Glass & Enamel, vol. 36, No. 1, Feb. 28, 2008, pp. 1-5 (including English-language abstract).

English-language translation of International Preliminary Report on Patentability (IPRP) dated Jun. 13, 2013 that issued in WO Patent Application No. PCT/JP2011/069836.

English-language translation of International Preliminary Report on Patentability (IPRP) dated Jun. 13, 2013 that issued in WO Patent Application No. PCT/JP2011/069838.

US 9,024,278 B2

QUANTUM-YIELD MEASUREMENT DEVICE

TECHNICAL FIELD

The present invention relates to a quantum-yield measurement device for measuring a quantum yield of a light-emitting material and the like by using an integrating sphere.

BACKGROUND ART

Known as a conventional quantum-yield measurement device is a technique which irradiates a sample such as a light-emitting material with pumping light, employs an integrating sphere to cause therein multiple reflections of a fluorescence emitted from the sample, and detects thus reflected light, so as to measure a quantum yield (ratio of "the number of photons of the fluorescence emitted from the light-emitting material" to "the number of photons of the pumping light absorbed by the light-emitting material") of the sample (see, for example, Patent Literatures 1 to 3).

When the sample is optically absorptive with respect to the fluorescent component in such a technique, there is a case where a part of the fluorescence is absorbed by the sample (which phenomenon will be referred to as "reabsorption" hereinafter). In such a case, the number of photons will be calculated smaller than the true number (i.e., the number of photons of the fluorescence actually emitted from the light-emitting material). It has therefore been proposed to use a fluorometer separately to measure the intensity of a fluorescence emitted from the sample in a state generating no reabsorption and correct according thereto the number of photons of the former fluorescence, so as to determine the quantum yield (see, for example, Non Patent Literature 1).

CITATION LIST

Patent Literature

Patent Literature 1: Japanese Patent Application Laid-Open No. 2007-086031
Patent Literature 2: Japanese Patent Application Laid-Open No. 2009-074866
Patent Literature 3: Japanese Patent Application Laid-Open No. 2010-151632

Non Patent Literature

Non Patent Literature 1: Christian Wurth and 7 others, "Evaluation of a Commercial Integrating Sphere Setup for the Determination of Absolute Photoluminescence Quantum Yields of Dilute Dye Solutions," APPLIED SPECTROSCOPY, (USA) Volume 64, Nov. 7, 2010, p. 733-741.

SUMMARY OF INVENTION

Technical Problem

As mentioned above, cumbersome operations such as using a fluorometer separately from a device equipped with an integrating sphere are required for accurately measuring the quantum yield of the sample by using the integrating sphere.

It is therefore an object of the present invention to provide a quantum-yield measurement device which can measure the quantum yield of the sample accurately and efficiently.

Solution to Problem

The quantum-yield measurement device in accordance with a first aspect of the present invention is a quantum-yield measurement device for measuring a quantum yield of a sample by irradiating a sample container of a sample cell for containing the sample with pumping light and detecting light to be measured emitted from at least one of the sample and sample container, the device comprising a dark box for arranging therein the sample container; a light generation unit, having a light exit part connected to the dark box, for generating the pumping light; a light detection unit, having a light entrance part connected to the dark box, for detecting the light to be measured; an integrating sphere, arranged within the dark box, having a light entrance opening for the pumping light to enter and a light exit opening for the light to be measured to exit; and a movement mechanism for moving the sample container, the light exit part, and the light entrance part such that the sample container attains each of a first state of being located inside of the integrating sphere and a second state of being located outside of the integrating sphere, and causing the light exit part to oppose the light entrance opening and causing the light entrance part to oppose the light exit opening, in the first state.

In this quantum-yield measurement device, the movement mechanism moves the sample container, the light exit part, and the light entrance part such that the sample container of the sample cell attains each of the first state of being located inside of the integrating sphere and the second state of being located outside of the integrating sphere. This makes it possible to detect a spectrum of a fluorescence (fluorescent component (the same hereinafter)) directly (without multiple reflections within the integrating sphere) in the second state and correct the spectrum of the fluorescence detected in the first state according to the spectrum of the fluorescence detected in the second state. Hence, this quantum-yield measurement device can measure the quantum yield of the sample accurately and efficiently.

The quantum-yield measurement device in accordance with a second aspect of the present invention is a quantum-yield measurement device for measuring a quantum yield of a sample by irradiating a sample container of a sample cell for containing the sample with pumping light and detecting light to be measured emitted from at least one of the sample and sample container, the device comprising a dark box for arranging therein the sample container; a light generation unit, having a light exit part connected to the dark box, for generating the pumping light; a light detection unit, having a light entrance part connected to the dark box, for detecting the light to be measured; an integrating sphere, arranged within the dark box, having a light entrance opening for the pumping light to enter and a light exit opening for the light to be measured to exit; and a movement mechanism for moving a plurality of parts configuring the integrating sphere such that the sample container attains each of a first state of being located inside of the integrating sphere and a second state of being located outside of the integrating sphere, and causing the light entrance opening to oppose the light exit part and causing the light exit opening to oppose the light entrance part, in the first state.

In this quantum-yield measurement device, the movement mechanism moves a plurality of parts constituting the integrating sphere such that the sample container of the sample cell attains each of the first state of being located inside of the integrating sphere and the second state of being located outside of the integrating sphere. This makes it possible to detect a spectrum of a fluorescence directly (without multiple reflections within the integrating sphere) in the second state and correct the spectrum of the fluorescence detected in the first state according to the spectrum of the fluorescence detected in the second state. Hence, this quantum-yield measurement device can measure the quantum yield of the sample accurately and efficiently.

The quantum-yield measurement device in accordance with a third aspect of the present invention is a quantum-yield measurement device for measuring a quantum yield of a sample by irradiating a sample container of a sample cell for containing the sample with pumping light and detecting light to be measured emitted from at least one of the sample and sample container, the device comprising a dark box for arranging therein the sample container; a light generation unit, having a light exit part connected to the dark box, for generating the pumping light; a light detection unit, having a light entrance part connected to the dark box, for detecting the light to be measured; a light-shielding member having a light entrance hole for the pumping light to enter and a light exit hole for the light to be measured to exit, and formed into such a shape as to cover the sample container; an integrating sphere, arranged within the dark box, having a light entrance opening for the pumping light to enter and a light exit opening for the light to be measured to exit, arranged within the dark box so as to cover the sample container in a state where the light entrance opening opposes the light exit part and the light exit opening opposes the light entrance part; and a movement mechanism for moving the light-shielding member such that the light-shielding member attains each of a first state of being located outside of the integrating sphere and a second state of being located inside of the integrating sphere and covering the sample container.

In this quantum-yield measurement device, the movement mechanism moves the light-shielding member such that the light-shielding member attains each of the first state of being located outside of the integrating sphere and the second state of being located inside of the integrating sphere and covering the sample container. This makes it possible to detect a spectrum of a fluorescence directly (without multiple reflections within the integrating sphere) in the second state and correct the spectrum of the fluorescence detected in the first state according to the spectrum of the fluorescence detected in the second state. Hence, this quantum-yield measurement device can measure the quantum yield of the sample accurately and efficiently.

The quantum-yield measurement device in accordance with a fourth aspect of the present invention is a quantum-yield measurement device for measuring a quantum yield of a sample by irradiating a sample container of a sample cell for containing the sample with pumping light and detecting light to be measured emitted from at least one of the sample and sample container, the device comprising a dark box for arranging therein the sample container; a light generation unit, having a light exit part connected to the dark box, for generating the pumping light; a light detection unit, having a light entrance part connected to the dark box, for detecting the light to be measured; an integrating sphere, having a light entrance opening for the pumping light to enter and a light exit opening for the light to be measured to exit, arranged within the dark box so as to cover the sample container in a state where the light entrance opening opposes the light exit part and the light exit opening opposes the light entrance part; a light guide system for directly guiding the light to be measured emitted from the sample to the light detection unit; and an optical path switching mechanism for switching an optical path of the light to be measured such that the light to be measured attains each of a first state of entering the light detection unit through the light exit opening and a second state of entering the light detection unit through the light guide system.

In this quantum-yield measurement device, the optical path switching mechanism switches the optical path of the light to be measured such that the light to be measured attains each of the first state of entering the light detection unit through the light exit opening and the second state of entering the light detection unit through the light guide system. This makes it possible to detect a spectrum of a fluorescence directly (without multiple reflections within the integrating sphere) in the second state and correct the spectrum of the fluorescence detected in the first state according to the spectrum of the fluorescence detected in the second state. Hence, this quantum-yield measurement device can measure the quantum yield of the sample accurately and efficiently.

The quantum-yield measurement device in accordance with a fifth aspect of the present invention is a quantum-yield measurement device for measuring a quantum yield of a sample by irradiating a sample container of a sample cell for containing the sample with pumping light and detecting light to be measured emitted from at least one of the sample and sample container, the device comprising a dark box for arranging therein the sample container; a light generation unit, having a light exit part connected to the dark box, for generating the pumping light; a light detection unit, having a light entrance part connected to the dark box, for detecting the light to be measured; an integrating sphere, having a light entrance opening for the pumping light to enter and a light exit opening for the light to be measured to exit, arranged within the dark box so as to cover the sample container in a state where the light entrance opening opposes the light exit part and the light exit opening opposes the light entrance part; a light guide system for directly guiding the pumping light to the sample container and directly guiding the light to be measured emitted from the sample to the light detection unit; and an optical path switching mechanism for switching an optical path of the pumping light an optical path of the light to be measured such as to attain each of a first state where the pumping light irradiates the sample container through the light entrance opening while the light to be measured enters the light detection unit through the light exit opening and a second state where the pumping light irradiates the sample container through the light guide system while the light to be measured enters the light detection unit through the light guide system.

In this quantum-yield measurement device, the optical path switching mechanism switches the optical path of the light to be measured and the optical path of the pumping light such as to attain each of the first state where the pumping light irradiates the sample container while the light to be measured enters the light detection unit through the light exit opening and the second state where the pumping light irradiates the sample container through the light guide system while the light to be measured enters the light detection unit through the light guide system. This makes it possible to detect a spectrum of a fluorescence directly (without multiple reflections within the integrating sphere) in the second state and correct the spectrum of the fluorescence detected in the first state according to the spectrum of the fluorescence detected in the second state. Hence, this quantum-yield measurement device can measure the quantum yield of the sample accurately and efficiently.

Advantageous Effects of Invention

The present invention can measure the quantum yield of the sample accurately and efficiently.

DESCRIPTION OF EMBODIMENTS

Figure 1:
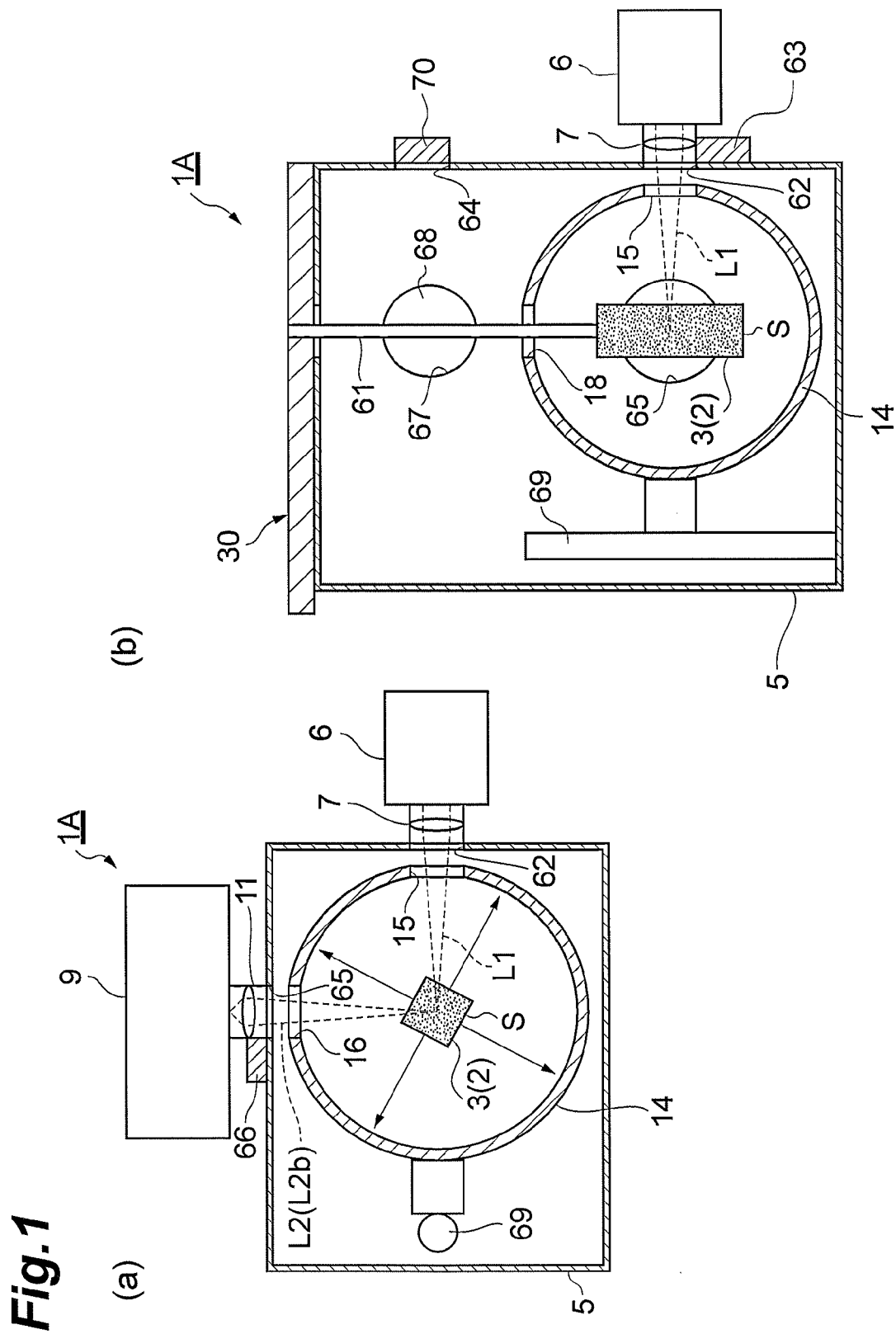
FIG. 1 is a set of transverse (a) and longitudinal (b) sectional views of the quantum-yield measurement device in accordance with a first embodiment of the present invention.

In the following, preferred embodiments of the present invention will be explained in detail with reference to the drawings. In the drawings, the same or equivalent parts will be referred to with the same signs while omitting their overlapping descriptions.

First Embodiment

FIG. 1 is a set of transverse (a) and longitudinal (b) sectional views of the quantum-yield measurement device in accordance with the first embodiment of the present invention. As FIG. 1 illustrates, the quantum-yield measurement device 1A is a device for measuring a quantum yield (light-emitting quantum yield, fluorescent quantum yield, phosphorescence quantum yield, or the like) of a sample S by irradiating a sample container 3 of a sample cell 2 for containing the sample S with pumping light L1 and detecting light to be measured L2 emitted from at least one of the sample S and sample container 3. An example of the sample S is one in which a light-emitting material or the like used for a light-emitting device such as that of organic EL is dissolved in a predetermined solvent. The sample cell 2 is made of synthetic silica, for example, while the sample container 3 is a quadrangular prism vessel, for example.

The quantum-yield measurement device 1A is equipped with a dark box 5 for arranging therein the sample container 3. The dark box 5 is a rectangular parallelepiped box made of a metal and blocks light from entering from the outside. The dark box 5 has an inner surface coated with a material which absorbs the pumping light L1 and the light to be measured L2, and so forth.

A light exit part 7 of a light generation unit 6 is connected to one side wall of the dark box 5. The light generation unit 6 is a pumping light source constituted by a xenon lamp, a spectroscope, and the like, for example, and generates the pumping light L1. The pumping light L1 enters the dark box 5 through the light exit part 7.

A light entrance part 11 of a light detection unit 9 is connected to a rear wall of the dark box 5. The light detection unit 9 is a multichannel detector constituted by a spectroscope, a CCD sensor, or the like, for example, and detects the light to be measured L2. The light to be measured L2 enters the light detection unit 9 through the light entrance part 13.

An integrating sphere 14 is arranged within the dark box 5 and secured to a predetermined position with a support pole 69. The integrating sphere 14 has an inner surface 14a coated with a highly diffusive reflecting agent such as barium sulfate or is formed from a material such as PTFE or Spectralon. The integrating sphere 14 is formed with a light entrance opening 15 for the pumping light L1 to enter and a light exit opening 16 for the light to be measured L2 to exit. The pumping light L1 enters the integrating sphere 14 through the light entrance opening 15. The light to be measured L2 is emitted out of the integrating sphere 14 through the light exit opening 16.

The foregoing dark box 5, light generation unit 6, and light detection unit 9 are contained in a housing made of a metal. The optical axis of the pumping light L1 emitted from the light exit part 7 of the light generation unit 6 and the optical axis of the light to be measured L2 made incident on the light entrance part 11 of the light detection unit 9 are substantially orthogonal to each other within a horizontal plane.

A cell insertion opening 18 for inserting therethrough the sample cell 2 is formed in the upper part of the integrating sphere 14. The sample cell 2 is held with a sample holding member 19 inserted through the cell insertion opening 18. A side face of the sample container 3 serving as a light entrance surface is tilted at a predetermined angle other than 90° with respect to the optical axis of the pumping light L1. This prevents the pumping light L1 reflected by the side face from returning to the light exit part 7.

The quantum-yield measurement device 1A further comprises a movement mechanism 30 for moving the sample container 3 of the sample cell 2, the light exit part 7 of the light generation unit 6, and the light entrance part 11 of the light detection unit 9. The movement mechanism 30 moves the sample container 3, light exit part 7, and light entrance part 11 such that the sample container 3 attains each of a first state of being located inside of the integrating sphere 14 and a second state of being located outside of the integrating sphere 14. The movement mechanism 30 causes the light exit part 7 of the light generation unit 6 and the light entrance part 11 of the light detection unit 9 to oppose the light entrance opening 15 and light exit opening 16 of the integrating sphere 14, respectively, in the first state.

In the first state, a shutter 63 is opened, so that the light exit part 7 faces into the dark box 5 through an opening 62 thereof, and a shutter 66 is opened, so that the light entrance part 11 faces into the dark box 5 through an opening 65 thereof. In the second state, on the other hand, a shutter 70 is opened, so that the light exit part 7 faces into the dark box 5 through an opening 64 thereof, and a shutter 68 is opened, so that the light entrance part 11 faces into the dark box 5 through an opening 67 thereof.

Figure 2:
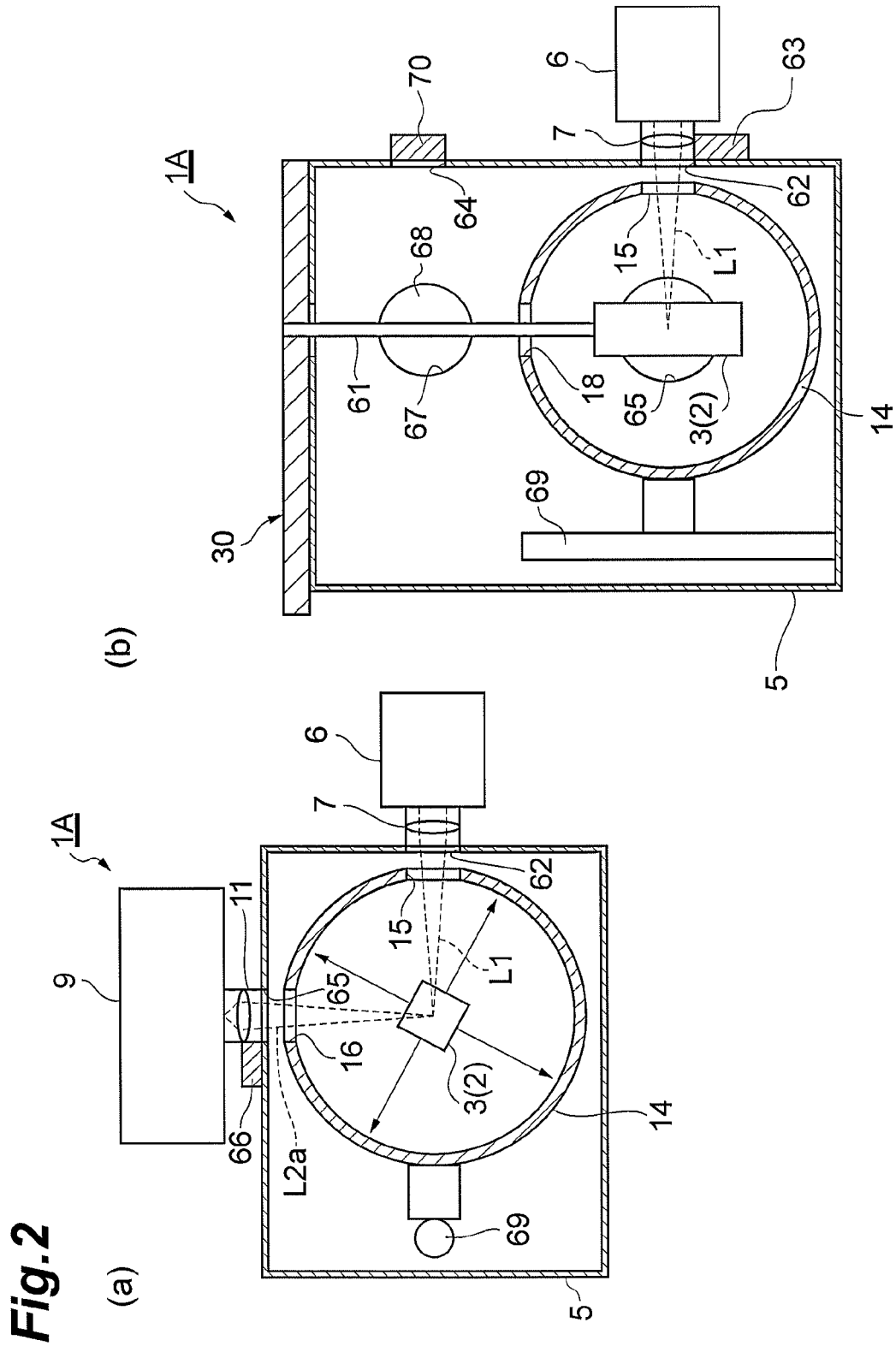
FIG. 2 is a set of transverse (a) and longitudinal (b) sectional views for explaining a method of measuring a quantum efficiency by using the quantum-yield measurement device of FIG. 1.

A method of measuring a quantum yield by using thus constructed quantum-yield measurement device 1A will now be explained. First, as FIG. 2 illustrates, an empty sample cell 2 not containing the sample S is set into the dark box 5. Subsequently, the sample container 3 in the first state of being located inside of the integrating sphere 14 is irradiated with the pumping light L1 emitted from the light generation unit 6. The parts of pumping light L1 reflected by and transmitted through the sample container 3 incur multiple reflections within the integrating sphere 14, so as to be detected by the light detection unit 9 as light to be measured L2a emitted from the sample container 3. Here, the shutters 63, 66 are opened, while the shutters 70, 68 are closed.

Next, as FIG. 1 illustrates, the sample cell 2 contains the sample S and is set into the dark box 5. Then, the sample container 3 in the first state of being located inside of the integrating sphere 14 is irradiated with the pumping light L1 emitted from the light generation unit 6. The part of pumping light L1 reflected by the sample container 3 and the fluorescence generated by the sample S incur multiple reflections within the integrating sphere 14, so as to be detected by the light detection unit 9 as light to be measured L2b emitted from the sample S and sample container 3. Here, the shutters 63, 66 are opened, while the shutters 70, 68 are closed.

Figure 3:
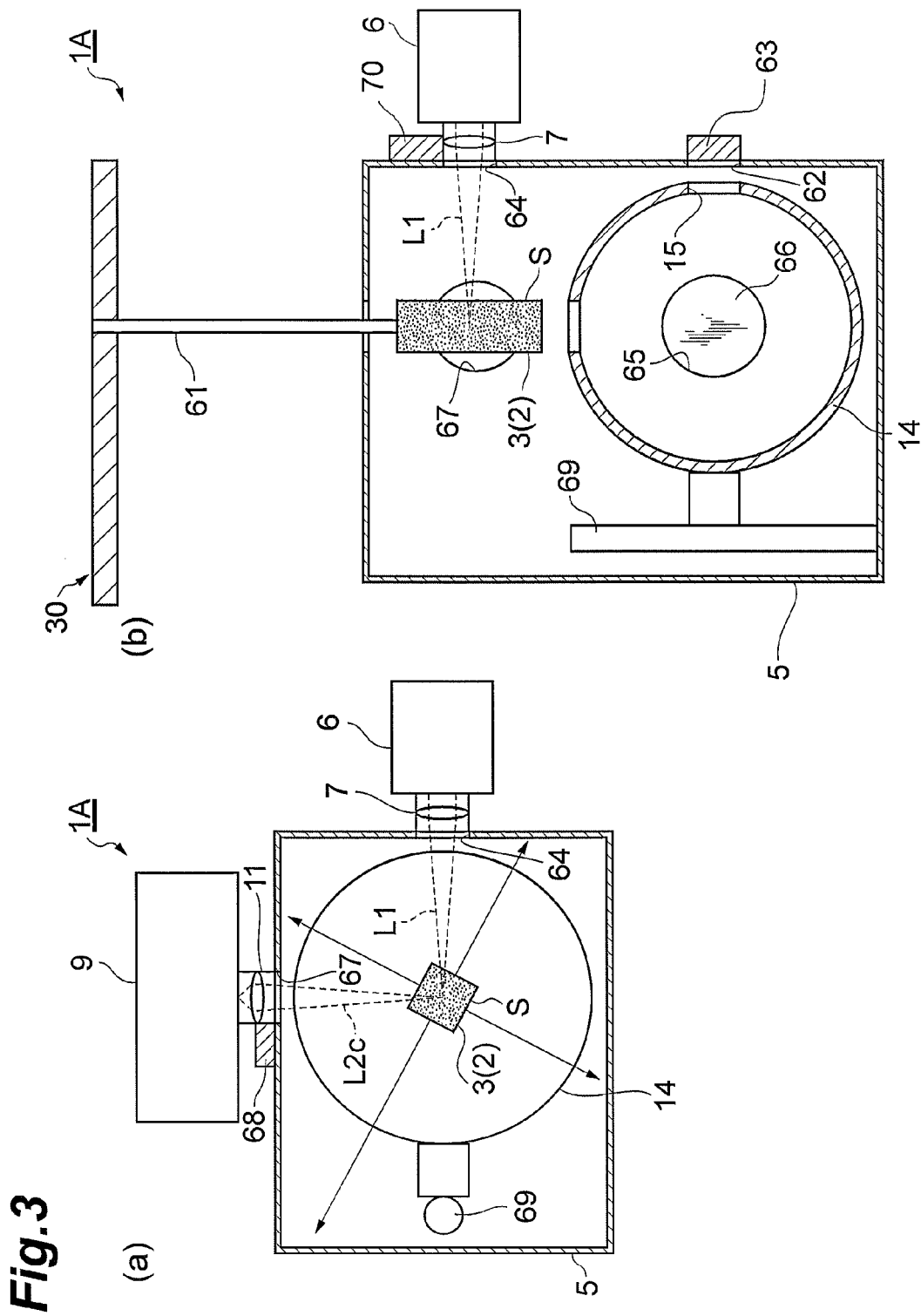
FIG. 3 is a set of transverse (a) and longitudinal (b) sectional views for explaining the method of measuring the quantum efficiency by using the quantum-yield measurement device of FIG. 1.

Subsequently, as FIG. 3 illustrates, the movement mechanism 30 moves (up, here) the sample container 3, light exit part 7, and light entrance part 11 such that the sample container 3 attains the second state of being located outside of the integrating sphere 14. Along with the change from the first state to the second state, the light entrance opening 15 and light exit opening 16 of the integrating sphere 14 move relative to the light exit part 7 of the light generation unit 6 and the light entrance part 11 of the light detection unit 9, respectively. Here, the sample container 3, light exit part 7, and light entrance part 11 hold their relative positional relationship. In the second state, the sample container 3 is irradiated with the pumping light L1 emitted from the light generation unit 6. The fluorescence generated by the sample S is detected directly (without multiple reflections within the integrating sphere 14) by the light detection unit 9 as light to be measured L2c emitted from the sample S. Here, the shutters 63, 66 are closed, while the shutters 70, 68 are opened.

Figure 4:
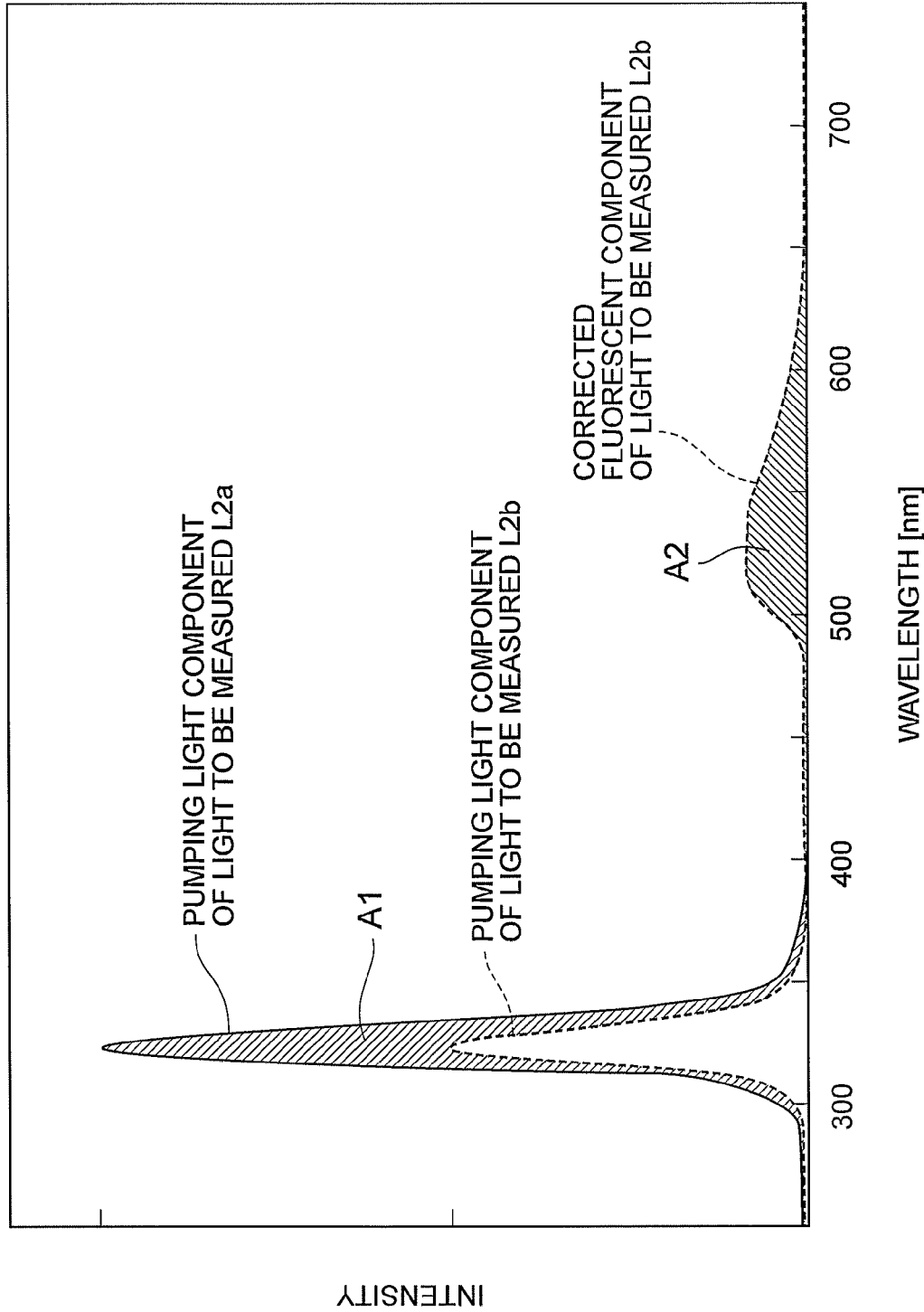
FIG. 4 is a graph for explaining the method of measuring the quantum efficiency by using the quantum-yield measurement device of FIG. 1.

When data of the light to be measured L2a, L2b, L2c are acquired as in the foregoing, a data analyzer such as a personal computer computes the number of photons (a value corresponding to the number of photons such as a value in proportion to the number of photons (the same hereinafter)) of pumping light L1 absorbed by the sample S according to data of the pumping light components of light to be measured L2a, L2b. The number of photons of pumping light L1 absorbed by the sample S corresponds to area A1 in FIG. 4.

On the other hand, the data analyzer corrects data of the fluorescent component of light to be measured L2b according to the data of light to be measured L2c (see Non Patent Literature 1 for details). As a consequence, even when the sample S is optically absorptive with respect to the fluorescent component, so that reabsorption occurs, the data analyzer computes the number of photons of fluorescence corrected so as to become the true number (i.e., the number of photons of the fluorescence actually emitted from the sample S). The number of photons of fluorescence emitted from the sample S corresponds to area A2 in FIG. 4.

Then, the data analyzer computes the quantum yield of the sample S, which is the ratio of "the number of photons of fluorescence emitted from the sample S" to "the number of photons of pumping light absorbed by the sample S." There is also a case where a solvent not dissolving the sample S therein is contained in the sample cell 2, which is set into the dark box 5, so that the light to be measured L2a is detected in the first state.

In the quantum-yield measurement device 1A, as explained in the foregoing, the movement mechanism 30 moves the sample container 3, light exit part 7, and light entrance part 11 such that the sample container 3 of the sample cell 2 attains each of the first and second states of being located inside and outside of the integrating sphere 14, respectively. This makes it possible to detect the number of photons of fluorescence directly (without multiple reflections within the integrating sphere 14) in the second state and correct the number of photons of fluorescence detected in the first state according to the number of photons of fluorescence detected in the second state. Hence, the quantum-yield measurement device 1A can measure the quantum yield of the sample S accurately and efficiently.

Figure 5:
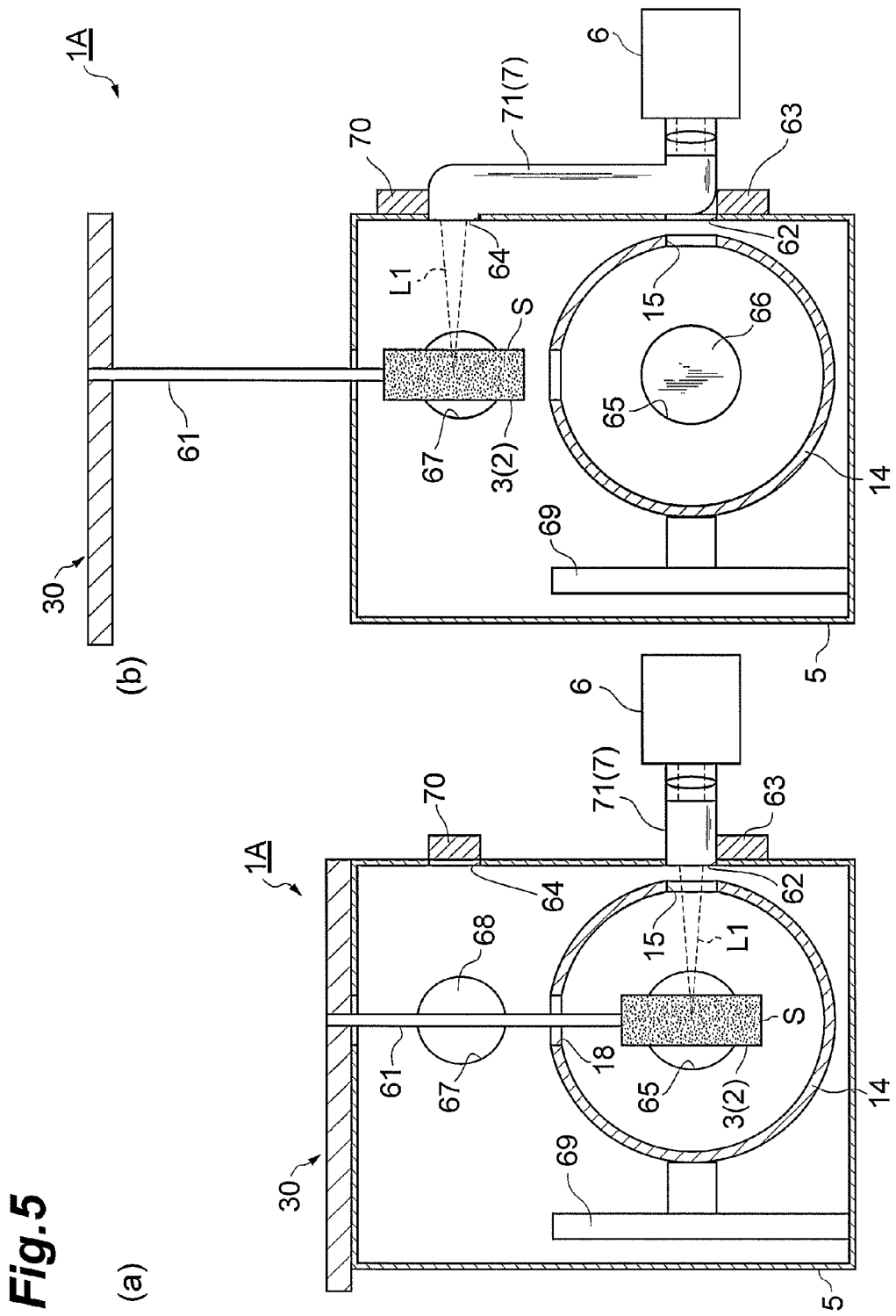
FIG. 5 is a set of longitudinal sectional views of a modified example of the quantum-yield measurement device in accordance with the first embodiment of the present invention.

The present invention is not limited to the first embodiment thereof explained in the foregoing. For example, as FIG. 5 illustrates, optical fibers 71 may optically connect the light generation unit 6 and the dark box 5 to each other and the light detection unit 9 and the dark box 5 to each other. In this case, moving the respective optical fibers 71 as the light exit part 7 and light entrance part 11 makes it unnecessary to move the light generation unit 6 and light detection unit 9.

Second Embodiment

Figure 6:
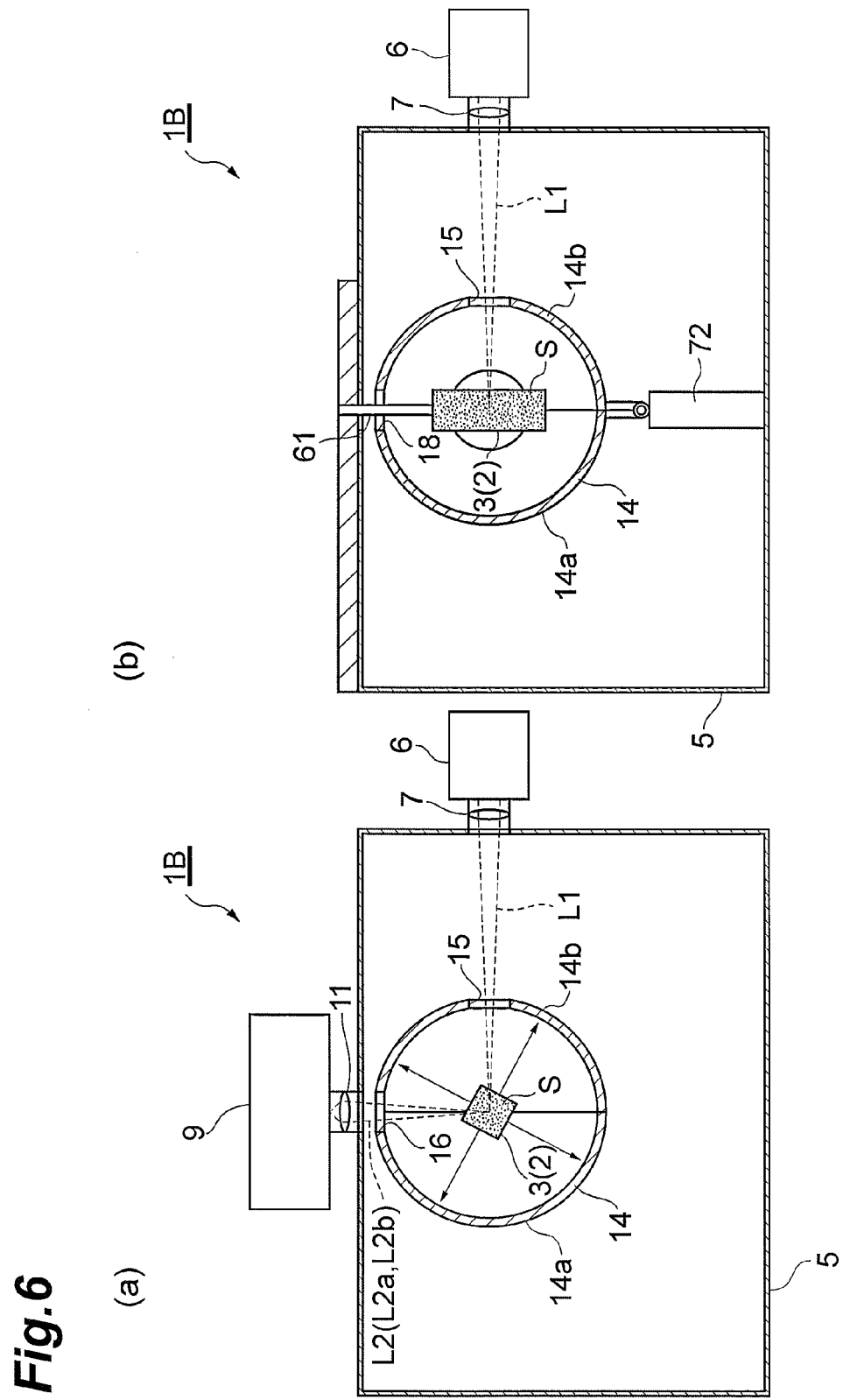
FIG. 6 is a set of transverse (a) and longitudinal (b) sectional views of the quantum-yield measurement device in accordance with a second embodiment of the present invention.

FIG. 6 is a set of transverse (a) and longitudinal (b) sectional views of the quantum-yield measurement device in accordance with the second embodiment of the present invention. As FIG. 6 illustrates, this quantum-yield measurement device 1B differs from the above-mentioned quantum-yield measurement device 1A mainly in that it is equipped with a movement mechanism 72 for moving a plurality of parts 14a, 14b constituting an integrating sphere 14.

The movement mechanism 72 supports the integrating sphere 14 within the dark box 5 and opens and closes a plurality of parts 14a, 14b constituting the integrating sphere 14. The parts 14a, 14b are hemispheres split along a plane which is substantially perpendicular to the optical axis of the pumping light L1 and substantially parallel to the optical axis of the light to be measured L2. The movement mechanism 72 opens the parts 14a, 14b such that their inner surfaces face up. The movement mechanism 72 closes the parts 14a, 14b such that the light entrance opening 15 and light exit opening 16 of the integrating sphere 14 oppose the light exit part 7 of the light generation unit 6 and the light entrance part 11 of the light detection unit 9, respectively.

A method of measuring a quantum yield by using the quantum-yield measurement device 1B will now be explained. First, an empty sample cell 2 not containing the sample S is set into the dark box 5. Subsequently, the sample container 3 in a first state of being located inside of the integrating sphere 14 (i.e., the state of FIG. 6 in which the parts 14a, 14b are closed) is irradiated with the pumping light L1 emitted from the light generation unit 6. The parts of pumping light L1 reflected by and transmitted through the sample container 3 incur multiple reflections within the integrating sphere 14, so as to be detected by the light detection unit 9 as light to be measured L2a emitted from the sample container 3.

Next, as FIG. 6 illustrates, the sample cell 2 contains the sample S and is set into the dark box 5. Then, the sample container 3 in the first state of being located inside of the integrating sphere 14 (i.e., the state where the parts 14a, 14b are closed) is irradiated with the pumping light L1 emitted from the light generation unit 6. The part of pumping light L1 reflected by the sample container 3 and the fluorescence generated by the sample S incur multiple reflections within the integrating sphere 14, so as to be detected by the light detection unit 9 as light to be measured L2b emitted from the sample S and sample container 3.

Figure 7:
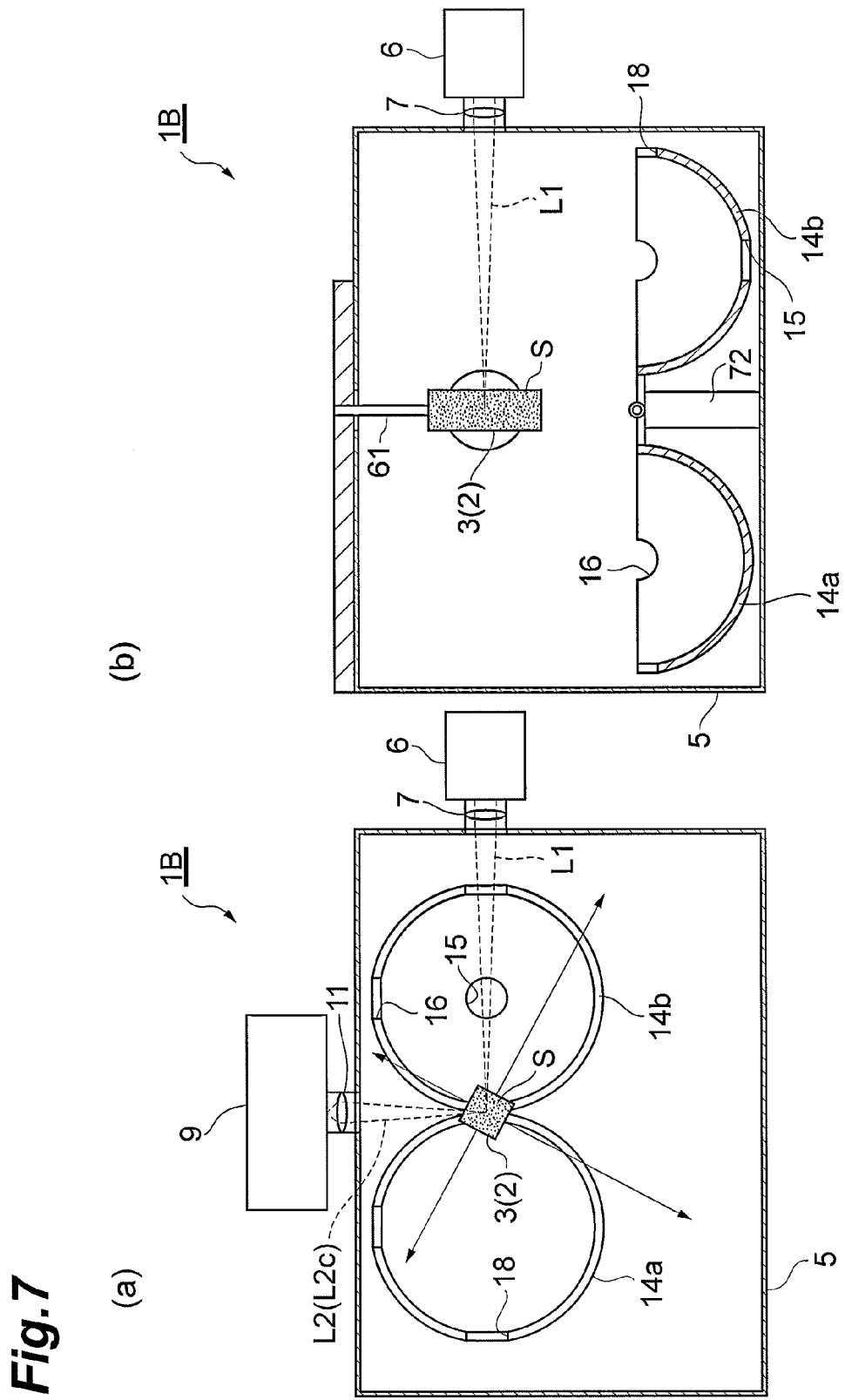
FIG. 7 is a set of transverse (a) and longitudinal (b) sectional views for explaining a method of measuring a quantum efficiency by using the quantum-yield measurement device of FIG. 6.

Subsequently, as FIG. 7 illustrates, the movement mechanism 72 moves the parts 14a, 14b such that the sample container 3 attains the second state of being located outside of the integrating sphere 14. In a second state (i.e., the state where the parts 14a, 14b are open), the sample container 3 is irradiated with the pumping light L1 emitted from the light generation unit 6. The fluorescence generated by the sample S is detected directly (without multiple reflections within the integrating sphere 14) by the light detection unit 9 as light to be measured L2c emitted from the sample S.

Thereafter, as with the above-mentioned quantum-yield measurement device 1A, a data analyzer computes the quantum yield of the sample S according to data of the light to be measured L2a, L2b, L2c.

In the quantum-yield measurement device 1B, as explained in the foregoing, the movement mechanism 72 moves a plurality of parts 14a, 14b constituting the integrating sphere 14 such that the sample container 3 of the sample cell 2 attains each of the first and second states of being located inside and outside of the integrating sphere 14, respectively. This makes it possible to detect the number of photons of fluorescence directly (without multiple reflections within the integrating sphere 14) in the second state and correct the number of photons of fluorescence detected in the first state according to the number of photons of fluorescence detected in the second state. Hence, the quantum-yield measurement device 1B can measure the quantum yield of the sample S accurately and efficiently.

In the second state, the parts 14a, 14b are opened in such directions that their inner surfaces do not oppose the light entrance part 11 of the light detection unit 9, which can inhibit the light to be measured L2 reflected by the inner surfaces of the parts 14a, if any, from entering the light entrance part 11.

The present invention is not limited to the second embodiment thereof explained in the foregoing. For example, the movement mechanism 72 may move three or more parts constituting the integrating sphere 14.

Third Embodiment

Figure 8:
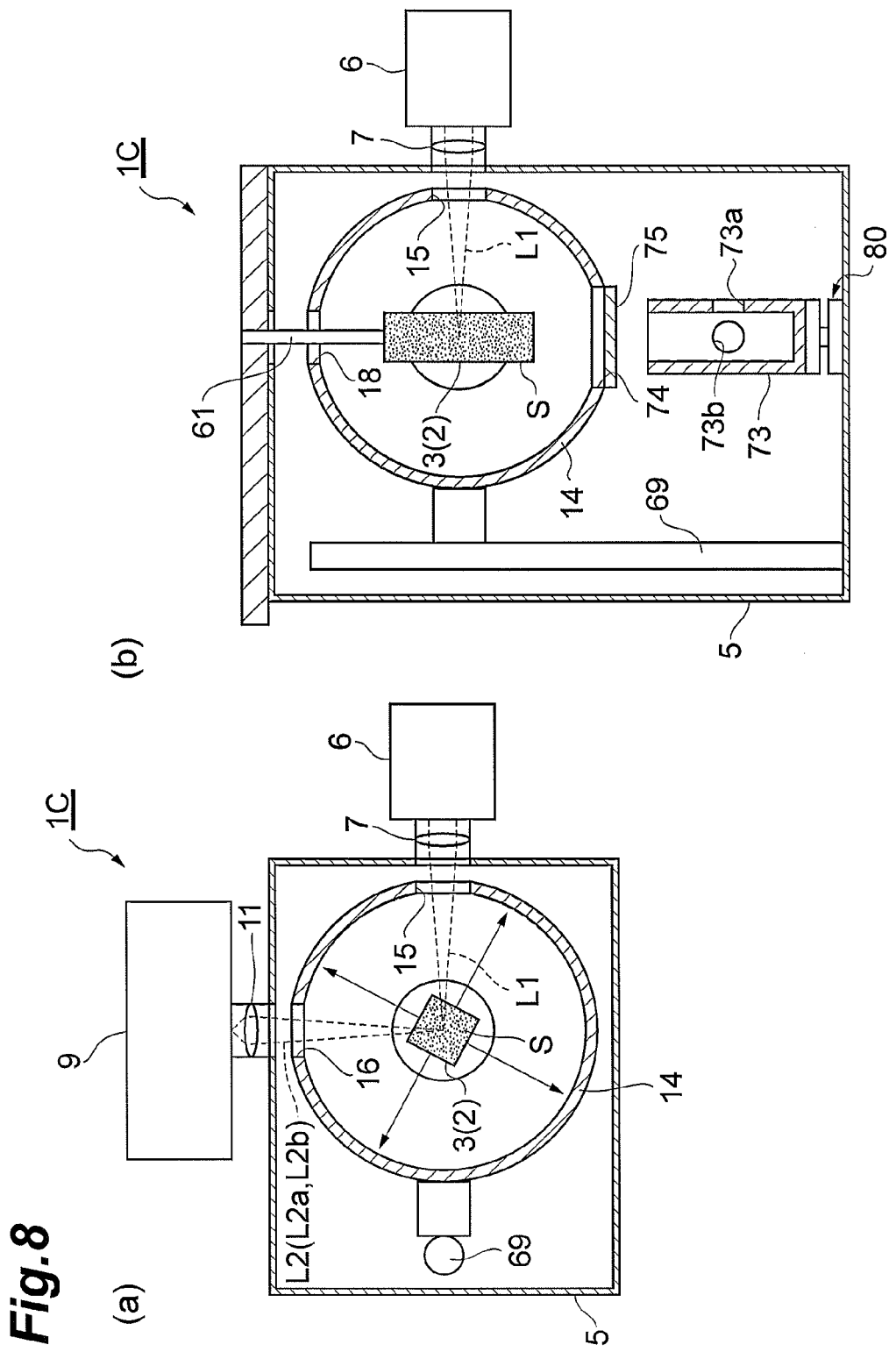
FIG. 8 is a set of transverse (a) and longitudinal (b) sectional views of the quantum-yield measurement device in accordance with a third embodiment of the present invention.

FIG. 8 is a set of transverse (a) and longitudinal (b) sectional views of the quantum-yield measurement device in accordance with the second embodiment of the present invention. As FIG. 8 illustrates, this quantum-yield measurement device 1C differs from the above-mentioned quantum-yield measurement device 1A mainly in that it is equipped with a light-shielding member 73 and a movement mechanism 80.

The light-shielding member 73 is formed into such a shape as to cover the sample container 3 and has a light entrance hole 73a for the pumping light L1 to enter and a light exit hole 73b for the light to be measured L2 to exit. The inner wall of the light-shielding member 73 is preferably processed with antireflection coating or the like. The movement mechanism 80 moves the light-shielding member 73 such that the light-shielding member 73 attains each of a first state of being located outside of the integrating sphere 14 and a second state of being located inside of the integrating sphere 14 and covering the sample container 3.

The integrating sphere 14 is arranged within the dark box 5 in a state where the light entrance opening 15 and light exit opening 16 oppose the light exit part 7 of the light generation unit 6 and the light entrance part 11 of the light detection unit 9, respectively. The integrating sphere 14 is formed with an opening 74 for inserting the light-shielding member 73 therethrough, while the opening 74 is provided with a shutter 75 for opening and closing the opening 74.

A method of measuring a quantum yield by using the quantum-yield measurement device 1C will now be explained. First, an empty sample cell 2 not containing the sample S is set into the dark box 5. Subsequently, in the first state where the light-shielding member 73 is located outside of the integrating sphere 14 (i.e., the state of FIG. 8), the sample container 3 is irradiated with the pumping light L1 emitted from the light generation unit 6. The parts of pumping light L1 reflected by and transmitted through the sample container 3 incur multiple reflections within the integrating sphere 14, so as to be detected by the light detection unit 9 as light to be measured L2a emitted from the sample container 3. Here, the shutter 75 is closed.

Next, as FIG. 8 illustrates, the sample cell 2 contains the sample S and is set into the dark box 5. Then, in the first state where the light-shielding member 73 is located outside of the integrating sphere 14, the sample container 3 is irradiated with the pumping light L1 emitted from the light generation unit 6. The part of pumping light L1 reflected by the sample container 3 and the fluorescence generated by the sample S incur multiple reflections within the integrating sphere 14, so as to be detected by the light detection unit 9 as light to be measured L2b emitted from the sample S and sample container 3. Here, the shutter 75 is closed.

Figure 9:
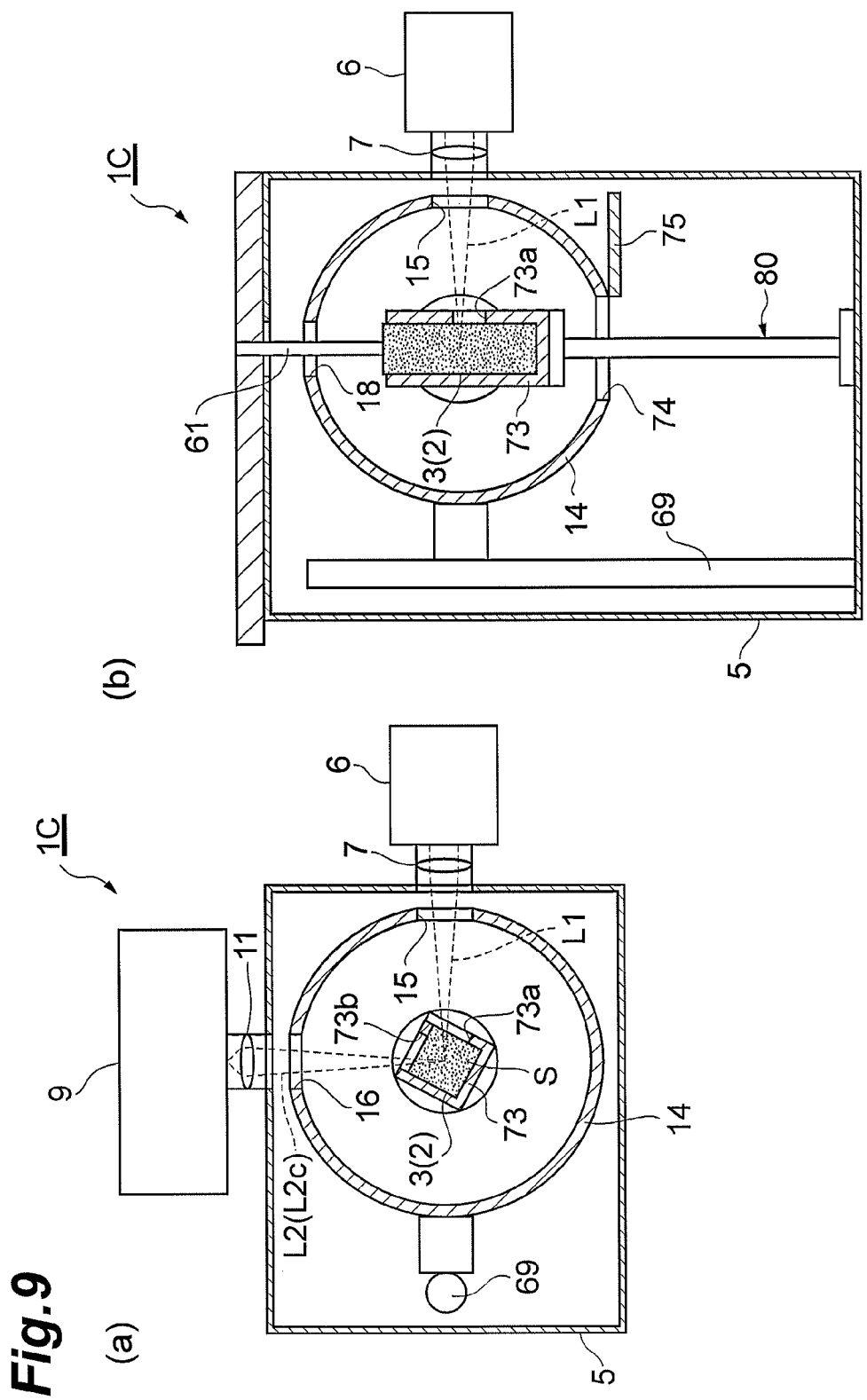
FIG. 9 is a set of transverse (a) and longitudinal (b) sectional views for explaining a method of measuring a quantum efficiency by using the quantum-yield measurement device of FIG. 8.

Subsequently, as FIG. 9 illustrates, the shutter 75 is opened, and the movement mechanism 80 moves the light-shielding member 73 such that the light-shielding member 73 attains the second state of being located within the integrating sphere 14 and covering the sample container 3. In the second state, the sample container 3 is irradiated with the pumping light L1 emitted from the light generation unit 6. The fluorescence generated by the sample S is detected directly (without multiple reflections within the integrating sphere 14) by the light detection unit 9 as light to be measured L2c emitted from the sample S. In the second state, the light entrance hole 73a and light exit hole 73b of the light-shielding member 73 oppose the light entrance opening 15 and light exit opening 16 of the integrating sphere 14, respectively.

Thereafter, as with the above-mentioned quantum-yield measurement device 1A, a data analyzer computes the quantum yield of the sample S according to data of the light to be measured L2a, L2b, L2c.

In the quantum-yield measurement device 1C, as explained in the foregoing, the movement mechanism 80 moves the light-shielding member 73 such that the light-shielding member 73 attains each of the first and second states of being located outside and inside of the integrating sphere 14, respectively. This makes it possible to detect the number of photons of fluorescence directly (without multiple reflections within the integrating sphere 14) in the second state and correct the number of photons of fluorescence detected in the first state according to the number of photons of fluorescence detected in the second state. Hence, the quantum-yield measurement device 1C can measure the quantum yield of the sample S accurately and efficiently.

Fourth Embodiment

Figure 10:
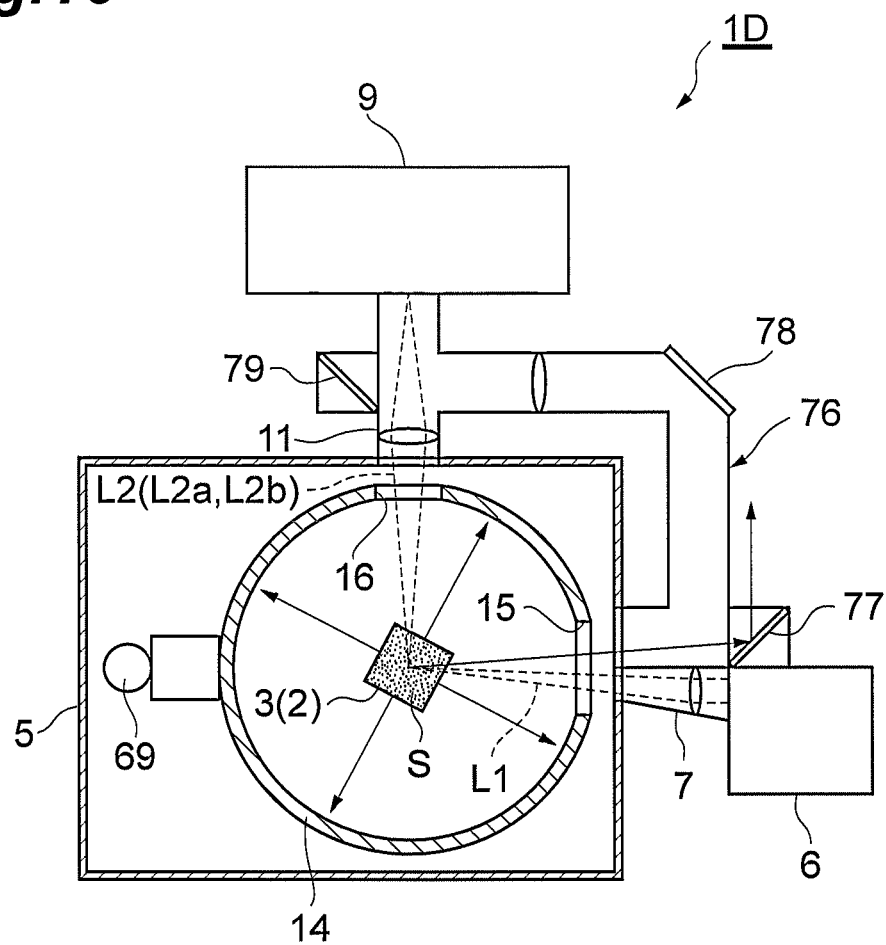
FIG. 10 is a transverse sectional view of the quantum-yield measurement device in accordance with a fourth embodiment of the present invention.

FIG. 10 is a transverse sectional view of the quantum-yield measurement device in accordance with the fourth embodiment of the present invention. As FIG. 10 illustrates, this quantum-yield measurement device 1D differs from the above-mentioned quantum-yield measurement device 1A mainly in that it is equipped with a light guide system 76 and optical path switching mechanisms 77, 79.

The light guide system 76 has an optical path extending from a position adjacent to a position connected to the light exit part 7 of the light generation unit 6 in the dark box 5 to a position in the light entrance part 11 of the light detection unit 9 and directly guides the light to be measured L2 emitted from the sample S to the light detection unit 9. The light guide system 76 has a mirror 78 for changing the direction of the optical path.

The optical path switching mechanism 77, which is a mirror adapted to advance to and retract from the optical path of the light guide system 76, reflects the light to be measured L2 entering the light guide system 76 onto the optical path of the light guide system 76 when located on the optical path. The optical path switching mechanism 79, which is a mirror adapted to advance to and retract from an intersection between the optical path of the light entrance part 11 and the optical path of the light guide system 76, reflects the light to be measured L2 guided by the light guide system 76 onto the optical path of the light entrance part 11 when located at the intersection. That is, the optical path switching mechanisms 76, 79 switch the optical path of the light to be measured L2 such as to attain each of first and second states where the light to be measured L2 enters the light detection unit 9 through the light exit opening 16 of the integrating sphere 14 and the light guide system 76, respectively.

The integrating sphere 14 is arranged within the dark box 5 such as to cover the sample container 3 in a state where the light entrance opening 15 and light exit opening 16 oppose the light exit part 7 of the light generation unit 6 and the light entrance part 11 of the light detection unit 9, respectively.

A method of measuring a quantum yield by using the quantum-yield measurement device 1D will now be explained. First, an empty sample cell 2 not containing the sample S is set into the dark box 5. Subsequently, in the first state where the light to be measured L2 enters the light detection unit 9 through the light exit opening 16 of the integrating sphere 14 (i.e., the state of FIG. 10), the sample container 3 is irradiated with the pumping light L1 emitted from the light generation unit 6. The parts of pumping light L1 reflected by and transmitted through the sample container 3 incur multiple reflections within the integrating sphere 14, so as to be detected by the light detection unit 9 as light to be measured L2a emitted from the sample container 3. Here, the optical path switching mechanism 77 is located outside of the light guide system 76, while the optical path switching mechanism 79 is located outside of the intersection between the optical path of the light entrance part 11 and the optical path of the light guide system 76.

Next, as FIG. 10 illustrates, the sample cell 2 contains the sample S and is set into the dark box 5. Then, in the first state where the light to be measured L2 enters the light detection unit 9 through the light exit opening 16 of the integrating sphere 14, the sample container 3 is irradiated with the pumping light L1 emitted from the light generation unit 6. The part of pumping light L1 reflected by the sample container 3 and the fluorescence generated by the sample S incur multiple reflections within the integrating sphere 14, so as to be detected by the light detection unit 9 as light to be measured L2b emitted from the sample S and sample container 3. Here, the optical path switching mechanism 77 is located outside of the light guide system 76, while the optical path switching mechanism 79 is located outside of the intersection between the optical path of the light entrance part 11 and the optical path of the light guide system 76.

Figure 11:
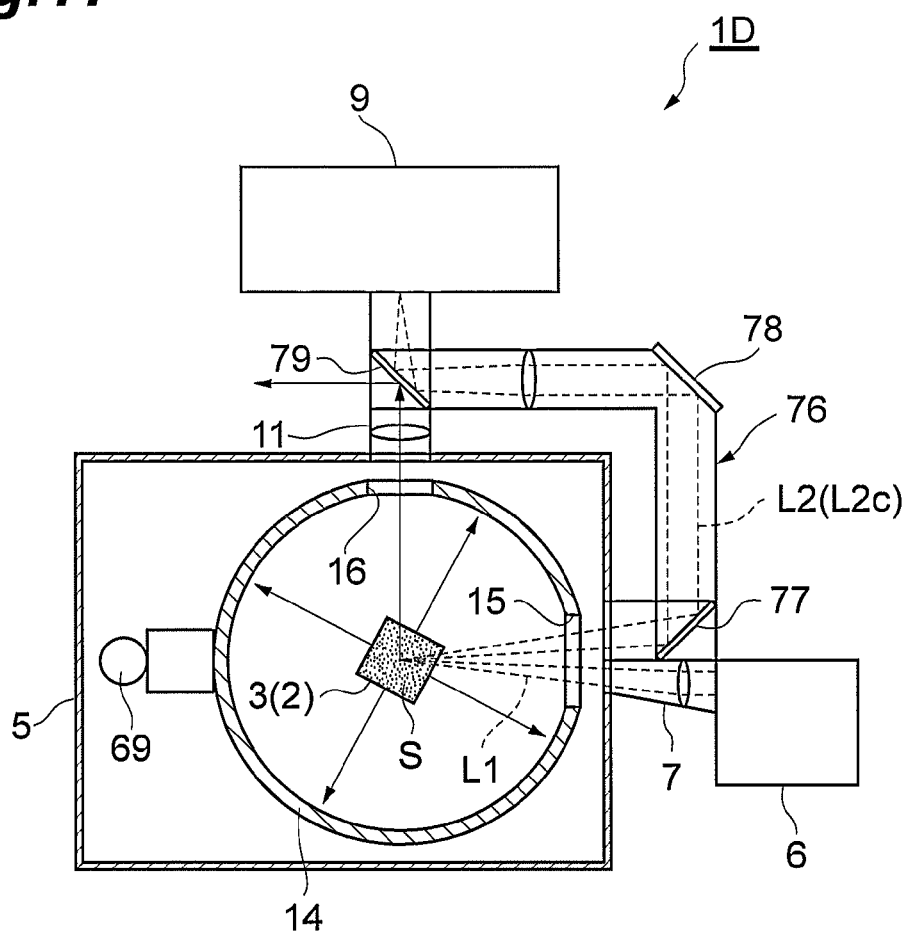
FIG. 11 is a transverse sectional view for explaining a method of measuring a quantum efficiency by using the quantum-yield measurement device of FIG. 10.

Subsequently, as FIG. 11 illustrates, the optical path switching mechanisms 77, 79 switch the optical path of the light to be measured L2 such as to attain the second state where the light to be measured L2 enters the light detection unit 9 through the light guide system 76. In the second state, the sample container 3 is irradiated with the pumping light L1 emitted from the light generation unit 6. The fluorescence generated by the sample S is detected directly (without multiple reflections within the integrating sphere 14) by the light detection unit 9 as light to be measured L2c emitted from the sample S. Here, the optical path switching mechanism 77 is located on the optical path of the light guide system 76, while the optical path switching mechanism 79 is located at the intersection between the optical path of the light entrance part 11 and the optical path of the light guide system 76.

Thereafter, as with the above-mentioned quantum-yield measurement device 1A, a data analyzer computes the quantum yield of the sample S according to data of the light to be measured L2a, L2b, L2c.

In the quantum-yield measurement device 1D, as explained in the foregoing, the optical path switching mechanisms 77, 79 switch the optical path of the light to be measured L2 such as to attain each of the first and second states where the light to be measured L2 enters the light detection unit 9 through the light exit opening 16 of the integrating sphere 14 and the light guide system 76, respectively. This makes it possible to detect the number of photons of fluorescence directly (without multiple reflections within the integrating sphere 14) in the second state and correct the number of photons of fluorescence detected in the first state according to the number of photons of fluorescence detected in the second state. Hence, the quantum-yield measurement device 1D can measure the quantum yield of the sample S accurately and efficiently.

Fifth Embodiment

Figure 12:
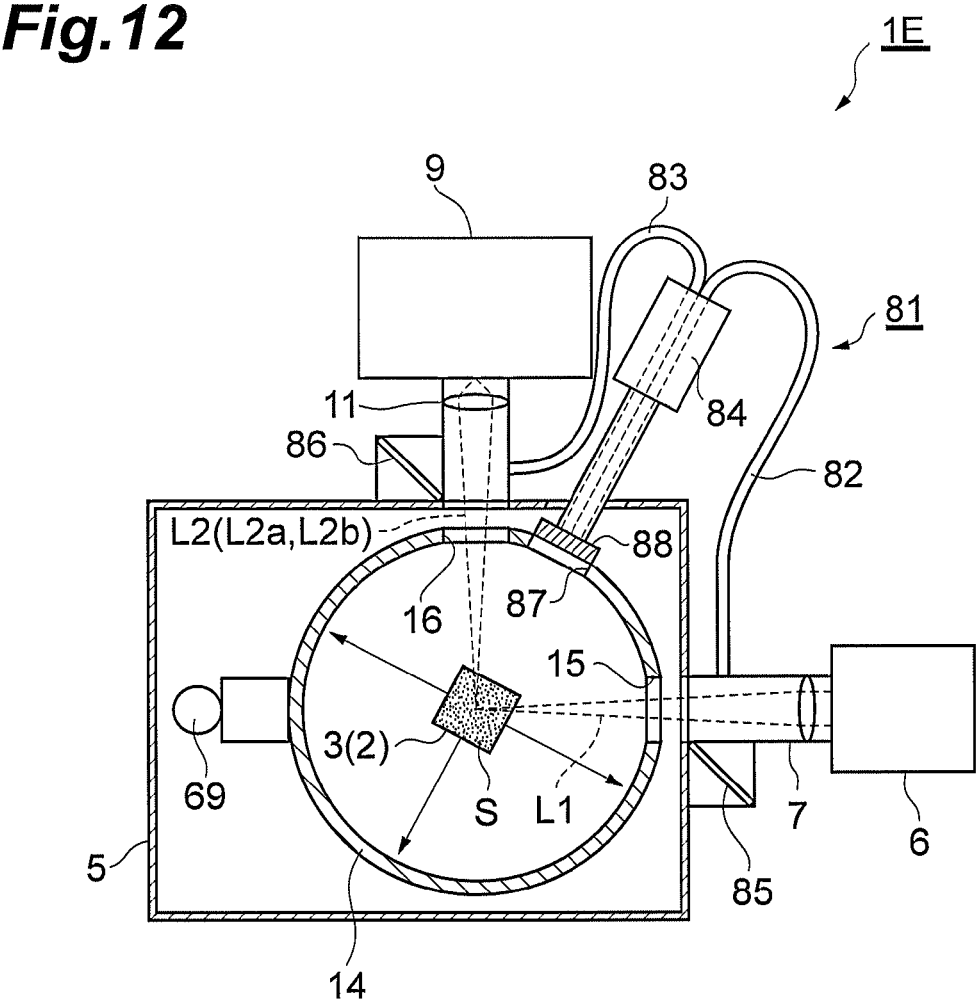
FIG. 12 is a transverse sectional view of the quantum-yield measurement device in accordance with a fifth embodiment of the present invention.

FIG. 12 is a transverse sectional view of the quantum-yield measurement device in accordance with the fifth embodiment of the present invention. As FIG. 12 illustrates, this quantum-yield measurement device 1E differs from the above-mentioned quantum-yield measurement device 1A mainly in that it is equipped with a light guide system 81 and optical path switching mechanisms 85, 86.

The light guide system 81 has an optical path extending from a position in the light exit part 7 of the light generation unit 6 to a position in the light entrance part 11 of the light detection unit 9 and directly guides the pumping light L1 to the sample container 3 and the light to be measured L2 emitted from the sample S to the light detection unit 9. The light guide system 81 has an optical fiber 82 for guiding the pumping light L1, an optical fiber 83 for guiding the light to be measured L2, and a fiber holding member 84 for bundling and holding a light exit end part of the optical fiber 82 and a light entrance part of the optical fiber 83. The fiber holding member 84 is adapted to advance to and retract from the sample container 3 through an opening 87 of the integrating sphere 14 which is opened and closed by a shutter 88.

The optical path switching mechanism 85 is a mirror which is adapted to retract from and advance to the optical path of the light exit part 7 and, when located on the optical path, reflects the pumping light L1 onto the optical path of the light guide system 81. The optical path switching mechanism 86 is a mirror which is adapted to retract from and advance to the optical path of the light entrance part 11 and, when located on the optical path, reflects the light to be measured L2 guided by the light guide system 81 onto the optical path of the light entrance part 11. That is, the optical path switching mechanisms 85, 86 switch the optical paths of the pumping light L1 and light to be measured L2 such as to attain each of a first state where the pumping light L1 irradiates the sample container 3 through the light entrance opening 15 while the light to be measured L2 enters the light detection unit 9 through the light exit opening 16 and a second state where the pumping light L1 irradiates the sample container 3 through the light guide system 81 while the light to be measured L2 enters the light detection unit 9 through the light guide system 81.

The integrating sphere 14 is arranged within the dark box 5 so as to cover the sample container 3 in a state where the light entrance opening 15 and light exit opening 16 oppose the light exit part 7 of the light generation unit 6 and the light entrance part 11 of the light detection unit 9, respectively.

A method of measuring a quantum yield by using the quantum-yield measurement device 1E will now be explained. First, an empty sample cell 2 not containing the sample S is set into the dark box 5. Subsequently, in the first state where the pumping light L1 irradiates the sample container 3 through the light entrance opening 15 while the light to be measured L2 enters the light detection unit 9 through the light exit opening 16 (i.e., the state of FIG. 12), the sample container 3 is irradiated with the pumping light L1 emitted from the light generation unit 6. The parts of pumping light L1 reflected by and transmitted through the sample container 3 incur multiple reflections within the integrating sphere 14, so as to be detected by the light detection unit 9 as light to be measured L2a emitted from the sample container 3. Here, the optical path switching mechanism 85 is located outside of the optical path of the light exit part 7, while the optical path switching mechanism 86 is located outside of the optical path of the light entrance part 11. The fiber holding member 84 is located outside of the integrating sphere 14, while the shutter 88 is closed.

Next, as FIG. 12 illustrates, the sample cell 2 contains the sample S and is set into the dark box 5. Then, in the first state where the pumping light L1 irradiates the sample container 3 through the light entrance opening 15 while the light to be measured L2 enters the light detection unit 9 through the light exit opening 16, the sample container 3 is irradiated with the pumping light L1 emitted from the light generation unit 6. The part of pumping light L1 reflected by the sample container 3 and the fluorescence generated by the sample S incur multiple reflections within the integrating sphere 14, so as to be detected by the light detection unit 9 as light to be measured L2b emitted from the sample S and sample container 3. Here, the optical path switching mechanism 85 is located outside of the optical path of the light exit part 7, while the optical path switching mechanism 86 is located outside of the optical path of the light entrance part 11. The fiber holding member 84 is located outside of the integrating sphere 14, while the shutter 88 is closed.

Figure 13:
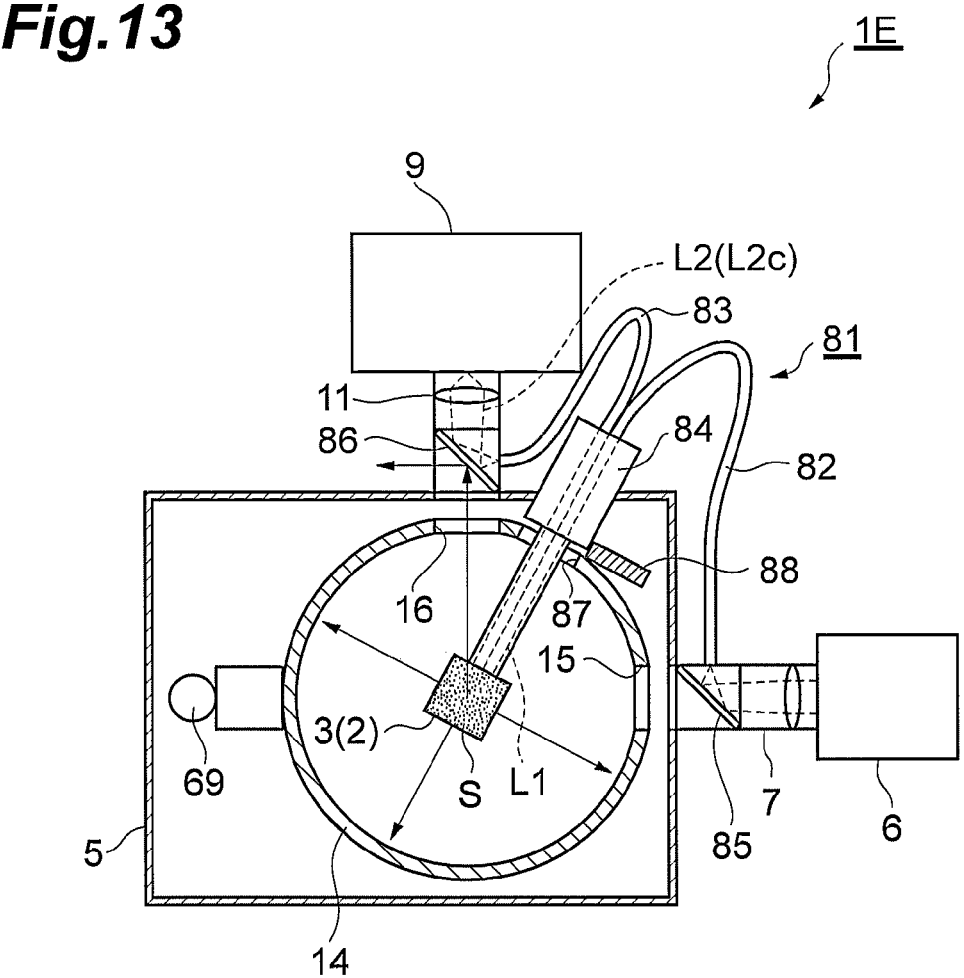
FIG. 13 is a transverse sectional view for explaining a method of measuring a quantum efficiency by using the quantum-yield measurement device of FIG. 12.

Subsequently, as FIG. 13 illustrates, the shutter 88 is opened, so that the fiber holding member 84 is allowed to come into contact with or approach the sample container 3 through the opening 87 of the integrating sphere 14. Further, the optical path switching mechanisms 85, 86 switch the optical paths of the pumping light L1 and light to be measured L2 such as to attain the second state where the pumping light L1 irradiates the sample container 3 through the light guide system 81 while the light to be measured L2 enters the light detection unit 9 through the light guide system 81. In the second state, the pumping light L1 is emitted from the light generation unit 6 and irradiates the sample container 3 through the optical fiber 82. The fluorescence generated by the sample S is detected directly (without multiple reflections within the integrating sphere 14) by the light detection unit 9 as light to be measured L2c emitted from the sample S. Here, the optical path switching mechanism 85 is located on the optical path of the light exit part 7, while the optical path switching mechanism 86 is located on the optical path of the light entrance part 11.

Thereafter, as with the above-mentioned quantum-yield measurement device 1A, a data analyzer computes the quantum yield of the sample S according to data of the light to be measured L2a, L2b, L2c.

In the quantum-yield measurement device 1E, as explained in the foregoing, the optical path switching mechanisms 85, 86 switch the optical paths of the pumping light L1 and light to be measured L2 such as to attain each of the first state where the pumping light L1 irradiates the sample container 3 through the light entrance opening 15 while the light to be measured L2 enters the light detection unit 9 through the light exit opening 16 and the second state where the pumping light L1 irradiates the sample container 3 through the light guide system 81 while the light to be measured L2 enters the light detection unit 9 through the light guide system 81. This makes it possible to detect the number of photons of fluorescence directly (without multiple reflections within the integrating sphere 14) in the second state and correct the number of photons of fluorescence detected in the first state according to the number of photons of fluorescence detected in the second state. Hence, the quantum-yield measurement device 1E can measure the quantum yield of the sample S accurately and efficiently.

INDUSTRIAL APPLICABILITY

The present invention can measure the quantum yield of the sample accurately and efficiently.

REFERENCE SIGNS LIST 1A, 1B, 1C, 1D, 1E . . . quantum-efficiency measurement device; 2 . . . sample cell; 3 . . . sample container; 5 . . . dark box; 6 . . . light generation unit; 7 . . . light exit part; 9 . . . light detection unit; 11 . . . light entrance part; 14 . . . integrating sphere; 15 . . . light entrance opening; 16 . . . light exit opening; 30, 72, 80 . . . movement mechanism; 73 . . . light-shielding member; 73a . . . light entrance hole; 73b . . . light exit hole; 76, 81 . . . light guide system; 77, 79, 85, 86 . . . optical path switching mechanism; L1 . . . pumping light; L2, L2a, L2b, L2c . . . light to be measured; S . . . sample

The invention claimed is:

1. A quantum-yield measurement device for measuring a quantum yield of a sample by irradiating a sample container of a sample cell for containing the sample with pumping light and detecting light to be measured emitted from at least one of the sample and sample container, the device comprising:
  a dark box configured to arrange therein the sample container;
  a light generation unit, having a light exit part connected to the dark box, configured to generate the pumping light;

a light detection unit, having a light entrance part connected to the dark box, configured to detect the light to be measured;

an integrating sphere, arranged within the dark box, having a light entrance opening for the pumping light to enter and a light exit opening for the light to be measured to exit; and a movement mechanism configured to move a plurality of parts configuring the integrating sphere such that the sample container attains each of a first state of being located inside of the integrating sphere and a second state of being located outside of the integrating sphere, and to cause the light entrance opening to oppose the light exit part and to cause the light exit opening to oppose the light entrance part, in the first state.

2. A quantum-yield measurement device for measuring a quantum yield of a sample by irradiating a sample container of a sample cell for containing the sample with pumping light and detecting light to be measured emitted from at least one of the sample and sample container, the device comprising:

a dark box configured to arrange therein the sample container;

a light generation unit, having a light exit part connected to the dark box, configured to generate the pumping light;

a light detection unit, having a light entrance part connected to the dark box, configured to detect the light to be measured;

a light-shielding member having a light entrance hole for the pumping light to enter and a light exit hole for the light to be measured to exit, and formed into such a shape as to cover the sample container;

an integrating sphere, having a light entrance opening for the pumping light to enter and a light exit opening for the light to be measured to exit, arranged within the dark box so as to cover the sample container in a state where the light entrance opening opposes the light exit part and the light exit opening opposes the light entrance part; and a movement mechanism configured to move the light-shielding member such that the light-shielding member attains each of a first state of being located outside of the integrating sphere and a second state of being located inside of the integrating sphere and covering the sample container.

3. A quantum-yield measurement device for measuring a quantum yield of a sample by irradiating a sample container of a sample cell for containing the sample with pumping light and detecting light to be measured emitted from at least one of the sample and sample container, the device comprising:

a dark box configured to arrange therein the sample container;

a light generation unit, having a light exit part connected to the dark box, configured to generate the pumping light;

a light detection unit, having a light entrance part connected to the dark box, configured to detect the light to be measured;

an integrating sphere, having a light entrance opening for the pumping light to enter and a light exit opening for the light to be measured to exit, arranged within the dark box so as to cover the sample container in a state where the light entrance opening opposes the light exit part and the light exit opening opposes the light entrance part;

a light guide system configured to directly guide the light to be measured emitted from the sample to the light detection unit; and an optical path switching mechanism configured to switch an optical path of the light to be measured such that the light to be measured attains each of a first state of entering the light detection unit through the light exit opening and a second state of entering the light detection unit through the light guide system.

4. A quantum-yield measurement device for measuring a quantum yield of a sample by irradiating a sample container of a sample cell for containing the sample with pumping light and detecting light to be measured emitted from at least one of the sample and sample container, the device comprising:

a dark box configured to arrange therein the sample container;

a light generation unit, having a light exit part connected to the dark box, configured to generate the pumping light;

a light detection unit, having a light entrance part connected to the dark box, configured to detect the light to be measured;

an integrating sphere, having a light entrance opening for the pumping light to enter and a light exit opening for the light to be measured to exit, arranged within the dark box so as to cover the sample container in a state where the light entrance opening opposes the light exit part and the light exit opening opposes the light entrance part;

a light guide system configured to directly guiding guide the pumping light to the sample container and directly guiding the light to be measured emitted from the sample to the light detection unit; and an optical path switching mechanism configured to switch an optical path of the pumping light and an optical path of the light to be measured such as to attain each of a first state where the pumping light irradiates the sample container through the light entrance opening while the light to be measured enters the light detection unit through the light exit opening and a second state where the pumping light irradiates the sample container through the light guide system while the light to be measured enters the light detection unit through the light guide system.

* * * * *